(12) United States Patent
McNaughton et al.

(10) Patent No.: US 8,033,898 B2
(45) Date of Patent: Oct. 11, 2011

(54) MICROBIOCIDAL CONTROL IN THE PROCESSING OF MEAT-PRODUCING FOUR-LEGGED ANIMALS

(75) Inventors: James L. McNaughton, Quantico, MD (US); Eric W. Liimatta, Baton Rouge, LA (US)

(73) Assignee: Albemarle Corporation, Baton Rouge, LA (US)

( * ) Notice: Subject to any disclaimer, the term of this patent is extended or adjusted under 35 U.S.C. 154(b) by 0 days.

(21) Appl. No.: 13/029,932

(22) Filed: Feb. 17, 2011

(65) Prior Publication Data
US 2011/0189338 A1 Aug. 4, 2011

Related U.S. Application Data

(60) Division of application No. 11/722,630, filed as application No. PCT/US2004/043732 on Dec. 23, 2004, now Pat. No. 7,901,276, which is a continuation-in-part of application No. 10/603,132, filed on Jun. 24, 2003, now abandoned.

(51) Int. Cl.
*A22C 18/00* (2006.01)

(52) U.S. Cl. ........................................... 452/149

(58) Field of Classification Search .................. 452/106, 452/125, 149, 150, 173, 198
See application file for complete search history.

(56) References Cited

U.S. PATENT DOCUMENTS

| | | | | |
|---|---|---|---|---|
| 4,849,237 A * | 7/1989 | Hurst | ............................ | 426/332 |
| 6,448,410 B1 * | 9/2002 | Howarth et al. | ............ | 548/320.5 |
| 6,638,959 B2 * | 10/2003 | Howarth et al. | .............. | 514/389 |
| 6,641,828 B1 * | 11/2003 | Howarth et al. | .............. | 424/405 |
| 6,680,070 B1 * | 1/2004 | Howarth et al. | .............. | 424/484 |
| 6,908,636 B2 * | 6/2005 | Howarth | ....................... | 426/310 |
| 6,919,364 B2 * | 7/2005 | Howarth et al. | .............. | 514/389 |
| 6,986,910 B2 * | 1/2006 | Howarth | ....................... | 426/310 |
| 7,172,782 B2 * | 2/2007 | Howarth | ....................... | 426/310 |
| 7,182,966 B2 * | 2/2007 | Howarth | ....................... | 426/310 |
| 7,371,397 B2 * | 5/2008 | Howarth et al. | .............. | 424/406 |
| 7,579,018 B2 * | 8/2009 | Howarth et al. | .............. | 424/406 |

* cited by examiner

*Primary Examiner* — Richard Price, Jr.

(74) *Attorney, Agent, or Firm* — Marcy M. Hoefling (57) ABSTRACT

Methods of processing four-legged slaughter animals for consumption as meat and/or meat product(s) are described. The methods comprise I) contacting exterior surfaces of the live animal at least once with a microbiocidal solution formed from mixing together at least (i) water and (ii) at least one 1,3-dibromo-5,5-dialkylhydantoin, such contacting occurring at least once when the animal is en route to being slaughtered but before it is killed by exsanguination; or II) contacting the carcass of the animal, after exsanguination, with a microbiocidal solution formed from mixing together at least (i) water and (ii) at least one 1,3-dibromo-5,5-dialkylhydantoin or III) contacting at least one raw meat product and/or at least one processed meat product derived from the carcass. The contacting can be done one or more times in each of I), II), and III). Considerable advantages, which are described, are realized when using such methods.

25 Claims, 2 Drawing Sheets

MICROBIOCIDAL CONTROL IN THE PROCESSING OF MEAT-PRODUCING FOUR-LEGGED ANIMALS

REFERENCE TO RELATED APPLICATIONS

This application is a divisional of U.S. application Ser. No. 11/722,630 filed on Jun. 22, 2007, which application is the National Stage of International Patent Application PCT/US2004/43732, filed on Dec. 23, 2004, which application is a continuation-in-part of co-pending U.S. application Ser. No. 10/603,132, filed Jun. 24, 2003, now abandoned, the disclosure of which is incorporated herein by reference.

Reference is hereby made to U.S. application Ser. No. 10/029,329, filed Dec. 21, 2001, now U.S. Pat. No. 6,908,636, issued Jun. 21, 2005, and to U.S. application Ser. No. 10/028,631, filed Dec. 21, 2001 now U.S. Pat. No. 6,919,364, issued Jul. 19, 2005, (presently owned by one of the two joint owners of the present application), both of which Applications are continuations-in-part of application Ser. No. 09/893,581, filed Jun. 28, 2001, now abandoned, and to U.S. application Ser. No. 10/313,245, filed Dec. 6, 2002, now U.S. Pat. No. 6,986,910, issued Jan. 17, 2006, which is a continuation-in-part of above-mentioned copending U.S. application Ser. No. 10/029,329, which in turn is a continuation-in-part of copending application Ser. No. 09/893,581, filed Jun. 28, 2001, now abandoned. Application Ser. No. 10/029,329 is owned by another party, and application Ser. No. 10/028,631 is presently owned by one of the two joint owners of the present application. Reference is also hereby made to PCT International Application No. PCT/US02/41479, filed Dec. 26, 2002, which is also presently owned by one of the two joint owners of the present application, in which the United States is one of the designated countries or regions, and to U.S. application Ser. No. 10/603,130, filed Jun. 24, 2003, now abandoned (presently owned by that other party). Three of these applications relate, inter alia, to use of 1,3-dibromo-5,5-dialkylhydantoins as treating agents for water used in the field of animal processing, while the fourth application relates, inter alia, to use of 1,3-dihalo-5,5-dialkylhydantoins other than 1,3-dibromo-5,5-dialkylhydantoins as treating agents for water used in the field of animal processing.

BACKGROUND

Contamination of meat and meat products with various pathogens such as species of *Listeria, Escherichia, Salmonella, Campylobacter*, and others, is a problem that has existed for many years. While various other microbiocidal materials have been investigated for efficacy, antimicrobial substances typically used in actual practice in animal processing in slaughterhouses have been certain acids or certain chlorine-based biocidal agents such as sodium hypochlorite and calcium hypochlorite.

Huge numbers of four-legged animals are slaughtered and processed for meat and meat products consumed either by humans or pets. Such animals include, for example, cattle, swine, horses, sheep, bison, rabbit, camel, kangaroo, alligator, crocodile, and other such existing or potential sources of meat products, such as buffalo, goats, and llamas. These and other four-legged meat-producing animals used for food and food products, e.g., deer, antelope, elk, squirrel, opossum, racoon, and nutria, are sometimes referred to collectively herein as four-legged slaughter animals. Also the term "cattle" is used in a generic sense to include steers, heifers, cows, calves, and bulls; "swine" is used in a generic sense to include hogs, sows, gilts, barrows, boars, and pigs; and the term "sheep" is used in a generic sense to include lambs, rams and ewes.

Many four-legged slaughter animals, especially those from which beef or pork are obtained, are processed by high-output meat packing plants using state-of-the-art technology. Despite modern processing procedures, bacterial contamination of fresh meat occurs as an undesirable but unavoidable result of converting live four-legged slaughter animals into food. Although current Good Manufacturing Procedures (GMPs) and/or recent government regulations can reduce this contamination, the total elimination of bacteria from fresh raw meats has not been achieved. Since deep muscle tissue is considered sterile in healthy animals, essentially all of the contamination originates from the carcass surfaces. Soil, dust and manure on the hair, hides and hooves of the animals represent one significant source of contamination. In addition, in some cases internal organs rupture during the removal process, resulting in further contamination of the carcass.

The general nature of the procedures and equipment used in the processing of four-legged slaughter animals for food is well-known to those of ordinary skill in the art. Indeed the literature in the field is extensive. For example, Outlines by G. R. Acuff, PhD, Professor of Food Microbiology, Texas A & M University, of a Pathogen Reduction Dialogue held May 6, 2002, describes a typical cattle slaughter operation as involving the following steps: Cattle Receiving & Holding, Stunning, Exsanguination, Head and Shank Removal, Hide Removal, Evisceration, Carcass Splitting, Final Wash, and Chill. For hog slaughter, Dr. Acuff, id., identifies the following steps: Hog Receiving & Holding, Stunning, Exsanguination, Scalding, Dehairing, Singeing, Scraping & Polishing, Evisceration, and Wash & Chill. Other authors give descriptions which are along the same general lines but which may vary to some extent. For example, slaughtering and processing of cattle as described in a chapter entitled *Overview of Meat Processing* refers in part to and explains the following processing steps: Pre-handling of cattle, Stunning and bleeding, Dressing and hide removal, Evisceration, and Cutting and boning. In addition, the chapter further explains that carcass cutting and boning often take place after chilling to but that recent developments have made it possible to undertake boning while the carcass is still warm, a method referred to as "hot boning". The same chapter describes and explains the steps in slaughtering and processing of pigs as including: Pre-handling of pigs, Stunning and bleeding, Dehairing and finishing, and Evisceration and splitting, with a statement in this latter section that, finally, the carcasses are chilled rapidly overnight before the subsequent processes of cutting and boning. Thus anyone unfamiliar with the steps or operations involved in the processing of four-legged slaughter animals for food can obtain a vast amount of information by reference to the extensive literature on the subject.

A number of the conventionally-used steps in the processing of four-legged slaughter animals for food constitute opportunities for microbial and pathogen contamination. A need thus exists for one or more new methods for reducing or eliminating such contamination of animal carcasses or parts thereof during the processing of four-legged slaughter animals for food. Another need is for the provision of one or more methods which do not involve excessive expense in reducing or eliminating such contamination. A further need is for the provision of one or more methods which do not involve undue interference with existing slaughterhouse and/or meat packing operations.

Besides fulfilling the foregoing needs, it is vitally important that the method used to fulfill the foregoing needs not cause any noticeable degradation in the quality or properties of the meat from the carcasses, especially in the appearance and taste of the meat.

This invention is deemed to enable fulfillment of the foregoing needs, and to cause no noticeable degradation in the quality or properties of the meat from the carcasses resulting from the use or the methods of this invention.

BRIEF SUMMARY OF THE INVENTION

This invention provides methods for decreasing microbial contamination of (I) a four-legged slaughter animal (for convenience hereinafter often referred to simply as "animal") being processed for slaughter and/or (II) the carcass of such animal and/or (III) raw meat products and/or processed meat products derived from the carcasses of such animals.

Pursuant to one embodiment of this invention, in the processing of a four-legged slaughter animal, the exterior surfaces of a live four-legged slaughter animal are contacted to prior to slaughter with an aqueous microbiocidal composition formed by mixing at least one 1,3-dibromo-5,5-dialkylhydantoin with an aqueous medium to form an aqueous microbiocidally-effective composition.

In another embodiment of this invention, at one or more suitable stages during the processing of the animal carcass, carcass surfaces of the slaughtered animal are contacted with an aqueous microbiocidal composition formed by mixing at least one 1,3-dibromo-5,5-dialkylhydantoin with an aqueous medium to form an aqueous microbiocidally-effective composition. Depending upon the type of animal carcass being processed, such contacting can be conducted before, during and/or after removing the hide from the carcass, or before or after removing the hair and/or bristles from the carcass.

In still another embodiment of this invention, at one or more suitable stages before, during and/or after the preparation of raw meat products and/or processed meat products such products are contacted with an aqueous microbiocidal composition formed by mixing at least one 1,3-dibromo-5,5-dialkylhydantoin with an aqueous medium to form an aqueous microbiocidally-effective composition. A few examples of raw meat products include steaks, chops, rib sections, meat roast cuts, hams, loins, animal organs, and ground meat. A few examples of processed meat products include ready-to-eat deli products, sausages, frankfurters, and sliced meats.

Substantial benefits can be achieved by the use of an aqueous microbiocidally-effective composition formed from one or more 1,3-dibromo-5,5-dialkylhydantoins. Besides being more effective on an equal halogen basis than other halogen-containing biocidal agents such as hypochlorite or N,N'-bromochloro-5,5-dimethylhydantoin, the 1,3-dibromo-5,5-dialkylhydantoins form aqueous microbiocidally-effective compositions that are less corrosive to the nozzles, fittings, cabinets, transporting apparatus, and other parts of the various washing, showering, spraying, and/or misting systems used. Moreover, because of their greater effectiveness as antimicrobials, 1,3-dibromo-5,5-dialkylhydantoins such as 1,3-dibromo-5,5-dimethylhydantoin can be introduced into an aqueous medium at suitably low dosage levels and yet form compositions having enhanced microbiocidal effectiveness, and with no appreciable adverse effect when applied to a live four-legged slaughter animal being processed for slaughter. In addition, the 1,3-dibromo-5,5-dialkylhydantoins form aqueous compositions that are stable over a range of temperatures from as low as just above the freezing point of the composition to about 70° C. and which throughout this temperature range are highly effective against microorganisms and pathogens even when such compositions are formed using low dosage levels of the 1,3-dibromo-5,5-dialkylhydantoin(s). Thus, the microbiocidally effective compositions of this invention can be effectively utilized under most, if not all, temperature conditions encountered in the processing of four-legged slaughter animals, at least for meat. Furthermore, experimental results have shown that, surprisingly, the practice of this invention will not cause noticeable degradation in the quality or properties of meat from the carcasses resulting from the use or methods of this invention. Thus the combination of extremely high antimicrobial effectiveness and lack of adverse effects upon meat enables the aqueous microbiocidally-effective composition formed from one or more 1,3-dibromo-5,5-dialkylhydantoins to also be effectively used in sanitizing raw meat and/or meat products at any stage before, during, and/or after their preparation.

Various embodiments and features of this invention will be further apparent from the ensuing description, accompanying drawings, and appended claims.

International Application WO 03/001931 A1, published 9 Jan. 2003 describes, inter alia, use of aqueous solutions of certain halogen based microbiocides such as a solution formed in water from bromine, chlorine or bromine chloride, or any two or all three thereof and a water-soluble source of sulfamate anion; or at least one 1,3-dihalo-5,5-dialkylhydantoin in which one of the halogen atoms is a chlorine atom and the other is a chlorine or bromine atom and the alkyls independently have 1-4 carbon atoms; or at least one 1,3-dibromo-5,5-dimethylhydantoin in which one alkyl is methyl, and the other alkyl has 1-4 carbon atoms to disinfect carcasses and/or parts of poultry resulting from the processing of poultry. It is shown that the color of chicken skin and the taste of the chicken meat are not adversely affected by the disinfection processing used. Processed carcasses of poultry have a coating of substantial water impervious skin covering the meat.

In contrast, carcasses of four-legged slaughter animals after removal of the hide, have no such water impervious protective coating. As will be seen hereinafter, it has been shown that direct contact of an aqueous microbiocidally-effective composition of this invention with raw beef produced only a slight change in the color of the meat indicating that the microbiocides used pursuant to this invention in appropriate proportions do not adversely affect the quality of the meat. Accordingly, the treatment of four-legged slaughter animals such as cattle with an aqueous microbiocidally-effective composition of this invention especially before hide removal, and/or carcasses of such animals after hide removal, should also have little, if any, effect upon the quality of the meat.

It is also noteworthy that poultry processing especially in modem highly automated plants, involves at least in the chill tank, long periods of time, e.g., an hour or so, during which the microbiocide can exert its microbiocidal activity. In contrast, in high-output meat packing plants and slaughterhouses in which cattle or pigs are processed, sprays of relatively short duration are typically used. Therefore, the time available for a microbiocide to exert its microbiocidal activity is usually considerably shorter in such plants or slaughterhouses than in a plant processing poultry for edible meat products.

FURTHER DETAILED DESCRIPTION OF THE INVENTION

The aqueous microbiocidally-effective compositions of this invention are formed from components comprised at least of (i) water and (ii) at least one 1,3-dibromo-5,5-dialkylhydantoin. These components are mixed in microbiocidally-effective proportions, and such proportions can vary depending on various factors such as for example the animal species being processed, the time of the year the animals are being processed, the amount of microbial contamination on the animals being processed, the kind and extent of contamination to which the animals, carcasses, and/or parts thereof are exposed during the various operations conducted in a slaughter house or meat packing plant, and the type of object(s) being processed or prepared, whether live animal, animal carcass, raw meat product, and/or processed meat product. In general, however, the components water and at least one 1,3-dibromo-5,5-dialkylhydantoin are proportioned such that an effective microbiocidal amount of microbiocide formed from water and the one or more 1,3-dibromo-5,5-dialkylhydantoins is present in the resultant composition. In forming such compositions, typically up to about 400 parts by weight of one or more 1,3-dibromo-5,5-dialkylhydantoins are mixed with one million parts by weight of water (i.e., the amount of 1,3-dibromo-5,5-dialkylhydantoin(s) used in forming the composition relative to the amount of water used in forming the composition is up to about 400 ppm wt/wt).

Preferred compositions are formed by mixing up to about 200 parts by weight, more preferably up to about 100 parts by weight, and still more preferably up to about 50 parts by weight, of one or more 1,3-dibromo-5,5-dialkylhydantoins per each million parts by weight of water used. Typically a minimum of at least about 0.5 part by weight of one or more 1,3-dibromo-5,5-dialkylhydantoins per each million parts by weight of water will be used in forming the aqueous microbiocidally-effective compositions of this invention, especially those compositions used for sanitizing or decontaminating raw meat products and/or processed meat products. Preferably at least about 10 parts by weight, more preferably at least about 20 parts by weight, and still more preferably at least about 50 parts by weight, of one or more 1,3-dibromo-5,5-dialkylhydantoins per each million parts by weight of water will be used in forming the aqueous microbiocidally-effective compositions of this invention, especially those compositions used for sanitizing or decontaminating live four-legged slaughter animals and/or carcasses of such animals. From the foregoing it will be seen that ranges of concentrations that may be used pursuant to this invention include the following: about 0.5 to about 400 ppm, about 0.5 to about 200 ppm, about 0.5 to about 100 ppm, about 0.5 to about 50 ppm, about 10 to about 400 ppm, about 10 to about 200 ppm, about 10 to about 100 ppm, about 10 to about 50 ppm, about 20 to about 400 ppm, about 20 to about 200 ppm, about 20 to about 100 ppm, about 20 to about 50 ppm, about 50 to about 400 ppm, about 50 to about 200 ppm, and about 50 to about 100 ppm. Particularly preferred especially for sanitizing or decontaminating live four-legged slaughter animals and/or carcasses of such animals are aqueous microbiocidally-effective compositions of this invention formed from an amount of one or more 1,3-dibromo-5,5-dialkylhydantoins in the range of about 20 to about 100 parts by weight per each million parts by weight of water. Preferred compositions used for sanitizing or decontaminating raw meat products and/or processed meat products are made from in the range of about 0.5 to about 400 parts by weight of one or more 1,3-dibromo-5,5-dialkylhydantoins per each million parts by weight of water. More preferred compositions for use in sanitizing or decontaminating raw meat products and/or processed meat products are made from in the range of about 50 to about 200 parts by weight of one or more 1,3-dibromo-5,5-dialkylhydantoins per each million parts by weight of water. Still more preferred compositions for use in sanitizing or decontaminating raw meat products and/or processed meat products are made from in the range of about 50 to about 100 parts by weight of one or more 1,3-dibromo-5,5-dialkylhydantoins per each million parts by weight of water.

Another way of expressing the amounts of one or more 1,3-dibromo-5,5-dialkylhydantoins that are dissolved in water to form an aqueous microbiocidally-effective composition of this invention is in terms of bromine residual. Thus in the practice of this invention the water is mixed with at least one 1,3-dibromo-5,5-dialkylhydantoin microbiocidal agent in an amount to achieve a bromine residual of up to about 400 ppm (wt/wt) as free bromine, preferably up to about 200 ppm (wt/wt) as free bromine More preferably, the amount of at least one 1,3-dibromo-5,5-dialkylhydantoin microbiocidal agent mixed with water achieves a bromine residual of up to about 100 ppm (wt/wt) as free bromine, and still more preferably up to about 50 ppm (wt/wt) as free bromine. Typically a minimum bromine residual of at least about 0.5 ppm (wt/wt) as free bromine from one or more 1,3-dibromo-5,5-dialkylhydantoins will be used especially in those compositions that are used for sanitizing or decontaminating raw meat products and/or processed meat products. Preferably a minimum bromine residual of at least about 10 ppm (wt/wt) as free bromine, more preferably of at least about 20 ppm (wt/wt) as free bromine, and still more preferably of at least about 50 ppm (wt/wt) as free bromine from one or more 1,3-dibromo-5,5-dialkylhydantoins will be used especially in those compositions that are used for sanitizing or decontaminating live four-legged slaughter animals and/or carcasses of such animals. Particularly preferred especially for sanitizing or decontaminating live four-legged slaughter animals and/or carcasses of such animals are aqueous microbiocidally-effective compositions of this invention having a bromine residual in the range of about 20 to about 100 ppm (wt/wt) as free bromine from one or more 1,3-dibromo-5,5-dialkylhydantoins. Preferred compositions used for sanitizing or decontaminating raw meat products and/or processed meat products are compositions having a bromine residual in the range of about 0.5 to about 400 ppm (wt/wt) as free bromine from one or more 1,3-dibromo-5,5-dialkylhydantoins. More preferred compositions for use in sanitizing or decontaminating raw meat products and/or processed meat products are compositions having a bromine residual in the range of about 50 to about 200 ppm (wt/wt) as free bromine from one or more 1,3-dibromo-5,5-dialkylhydantoins. Still more preferred compositions for use in sanitizing or decontaminating raw meat products and/or processed meat products are compositions having a bromine residual in the range of about 50 to about 100 ppm (wt/wt) as free bromine from one or more 1,3-dibromo-5,5-dialkylhydantoins. The product solution is typically used at a temperature of about 5 to about 39° C., but can be used at higher temperatures, e.g., up to about 70° C., if desired.

There are two general types of four-legged slaughter animal processing wherein this invention is applicable. They are:

I) administration of aqueous microbiocidally-effective compositions used pursuant to this invention to exterior surfaces of the live four-legged slaughter animals being processed for slaughter; and II) administration of aqueous microbiocidally-effective compositions used pursuant to this invention to the carcasses of freshly-slaughtered four-legged slaughter animals being processed for meat and/or meat products.

As noted above there is another category of processing wherein this invention is applicable, which is:

III) administration of aqueous microbiocidally-effective compositions used pursuant to this invention to the raw meat products and/or processed meat products derived from the slaughtered animal at any suitable stage(s) before, during, and/or after any operation used in the preparation and/or processing of such raw meat products and/or processed meat products.

Type I Processing

As can be seen from the above, Type I processing pursuant to this invention relates to reducing microbiocidal contamination of meat and/or meat products to be produced from the processing of the animals, by contacting exterior surfaces of the animal during one or more of the initial stages of the processing while the animal has not yet been killed. These stages include any pre-handling steps taken with the animals before they are killed (i.e., while they are still alive) such as receiving & holding the animal, moving the animal to the stunning area, stunning the animal, and handling or moving the stunned animal before exsanguination. Thus pursuant to an embodiment of this invention exterior surfaces of the animal are contacted with one or more aqueous microbiocidally-effective compositions of this invention during at least one such stage or step while the animal is still alive.

Preferably, prior to application of one or more microbiocidally-effective to compositions of this invention to the live animal, areas such as animal hind quarters, legs and hoofs and other areas where fecal matter exists on the animals, are initially cleansed of fecal matter by hosing or use of sprays of at least water or aqueous detergent solutions.

Whether or not such preferred cleansing is conducted, pursuant to this invention the live animal is exposed to spraying, showering, misting, partial bathing, or any other suitable method of applying at least one aqueous microbiocidally-effective composition of this invention to exterior surfaces of the animal while it is still alive. Preferably such at least one aqueous microbiocidally-effective composition of this invention is applied to substantially the entire animal before the animal enters the area where exsanguination (i.e., bleeding and thus killing) is to occur. This can be accomplished, for example, by providing at least one shower zone and/or spray zone at a location where the animals are caused to move from holding areas toward the slaughterhouse or meat packing plant. As the animals pass through such zone or zones, they are showered and/or sprayed with one or more aqueous microbiocidally-effective compositions of this invention so that the exterior of the animal becomes wetted by such composition. Such sprays can be fixed or articulated sprays. Also, the shower and/or sprays can be of different intensities so as ensure thorough wetting of the hide and flushing of debris from the animal. Preferably, the animal is then caused to walk through a bath of aqueous microbiocidally-effective composition of this invention so that at least the lower leg area and hoofs of the animal are washed by such composition. Such bath can include subsurface forced spray jets to improve washing efficiency. It is preferred to locate such bath outside of the slaughterhouse or meat packing plant, and/or at least in a perimeter area of the slaughterhouse or meat packing plant as such positioning will help ensure that the amount of microbiocidal contamination brought into the slaughterhouse or meat packing plant is effectively minimized by practice of this invention. This in turn greatly reduces the likelihood of cross contamination during subsequent processing operations conducted in the slaughterhouse or meat packing plant.

Another Type I operation pursuant to this invention is application of mists of aqueous microbiocidally-effective composition of this invention to the animal in lieu of, or in addition to, sprays as the animal moves toward the slaughterhouse or meat packing plant. Also the sequence of passage through zones can be varied, e.g., causing the animal(s) to walk through a bath of aqueous microbiocidally-effective composition can occur before or at the same time one or more showers and/or sprays are applied to the to animal. Another option is to provide a misting zone in which at least one aqueous microbiocidally-effective composition of this invention is applied to the animal after one or more zones where showering, spraying and/or bathing (in whatever sequence is desired) of the animal with at least one aqueous microbiocidally-effective composition of this invention take(s) place. In short, any sequence of applying at least one aqueous microbiocidally-effective composition of this invention to the live animal can be used. And such application preferably takes place as the animal is moved toward the slaughterhouse or meat packing plant and/or is in a perimeter area of the slaughterhouse or meat packing plant.

Still another embodiment of the invention is a novel way of applying one or more showers and/or sprays to the live animal. This is accomplished by utilizing a portable shower and/or spray stall which may also contain a misting and/or partial bathing zone. The animal or a procession of animals is caused to pass into and through such stall in which the exterior(s) of such animal(s) are contacted (e.g., showered, sprayed, etc.) with at least one aqueous microbiocidally-effective composition of this invention before proceeding into, or further into, the slaughterhouse or meat packing plant. Such portable shower or spray stall can be sized and adapted to be transported from one place to another by means of an 18-wheeler truck-trailer or railroad car, or can itself be constructed as a unitary suitably-wheeled trailer adapted to be transported from place to place by means of a truck tractor or farm tractor. Such trailer can be equipped with its own supply of aqueous microbiocidally-effective composition of this invention, or the trailer can draw from a supply of such composition located on the site where usage is to occur. Similarly, the power to drive the pumps which feed the aqueous microbiocidally-effective composition of this invention to the shower(s), sprays, and/or misting devices can be generated by an on board power supply or generator, or the power can be provided by the site where usage is to occur. Preferably, the waste water from use of such portable shower and/or spray stall is collected by the stall itself. After solids are removed from the recovered waste water and, if necessary, additional microbiocidally-effective composition of this invention is mixed with such solids-free waste water, the resultant waste water can be reused in the portable shower and/or spray stall. This embodiment is especially useful in the case of small abattoirs where, periodically, only one or a relatively small number of animals are slaughtered, as a portable shower and/or spray stall can be delivered from place to place for use at different small abattoirs when the animal slaughter operation is to take place therein.

Where more than one live animal bathing zone, showering zone, spray zone, and/or misting zone is used pursuant to this invention, the microbiocidally-effective concentrations of the respective aqueous microbiocidally-effective compositions of this invention used in such zones can be the same or at least two such compositions can differ in concentration. The actual concentration ranges are typically in the ranges described above but can be increased to suit the needs of the occasion, such as in cases where animals have been exposed to extraordinary amounts of fecal matter due to unusual circumstances such as unanticipated microbiocidal contamination of a supply of animal feed or drinking water, sickness of some animals within a herd, transportation delays, or the like.

The temperature(s) of the aqueous microbiocidally-effective composition(s) of this invention used in the above Type I processing pursuant to this invention can differ over a suitable range. Thus the composition(s) used can be applied after being heated to a suitable warm temperature or conversely cooled to a suitable cooling temperature to assist in calming the animals as they approach the slaughterhouse or meat packing plant, and thereby improve the movement of a procession of animals from the holding area to the slaughter house or meat packing plant and/or as they approach the stunning area. Also, by suitably adjusting the temperature of the composition(s) it is possible to prevent or at least reduce heat-related sickness (e.g., heat stroke) of stressed closely-packed animals.

Among additional advantages of the above Type I processing is that the microbiocidal effectiveness of the aqueous microbiocidal compositions formed by mixing one or more 1,3-dibromo-5,5-dialkylhydantoins with an aqueous medium is exceptionally high even when using low dosage levels of such compound(s). This in turn avoids or at least minimizes the likelihood of adverse behavioral reaction of the animal if and when, for example, the spray is applied to the eyes or otherwise comes into contact with sensitive body parts of the animal. Avoidance or minimization of such adverse behavioral reaction of the animal is beneficial in that the movement of a procession of animals to the slaughterhouse or meat packing plant and/or to the stunning area is not disrupted.

In small abattoir operations where, periodically, only one or a relatively few animals are slaughtered, the above-described operations can be conducted in various ways. For example, the animal(s) can be sprayed by use of one or more hand held pressurized spraying devices each attached by a hose to a suitable supply of an aqueous to microbiocidally-effective composition of this invention. Alternatively, the composition can be applied by use, for example, of mops, hand-held rags, sponges, or scrubbing brushes, and/or simply by splashing the live animal with the composition of this invention from a pail or bucket. In operations such as these, care should be taken to ensure that effective coverage of the exterior animal surfaces by the applied aqueous microbiocidally-effective composition of this invention is achieved. Also, as in any operation where portions of the operator(s) may be exposed over and over again to a chemical solution, it is desirable for the operator(s) to wear at least water-impermeable gloves and goggles, and preferably water-impermeable outer garments as well. As noted above, it is preferable to wash the animal with water before applying the aqueous microbiocidally-effective composition of this invention to the animal.

Other places in the slaughterhouse or meat packing plant where an aqueous microbiocidally-effective composition of this invention can be applied with desirable results to the animal while it is still alive are in the area where the animal is to be stunned and/or where the stunned animal is handled after stunning but before exsanguination is initiated. Such handling may include, for example, transporting and/or attaching the stunned animal to a conveyor system. At such locations in the slaughterhouse or meat packing plant, application of an aqueous microbiocidally-effective composition of this invention to exterior surfaces of the stunned animal such as by means of a shower system, spray system, misting system or bath can be advantageous. Such an operation can be used in addition to or in place of the application of an aqueous microbiocidally-effective composition of this invention to exterior surfaces of the animal as it moves from the holding area toward the slaughterhouse or meat packing plant and/or is in a perimeter area of the slaughterhouse or meat packing plant, as described above. In all cases of Type I processing, it is preferred to ensure that the live animal has been thoroughly washed with water or aqueous detergent solution at least once before applying the aqueous microbiocidally-effective composition of this invention to the animal before it is killed.

It is also possible pursuant to this invention to wash the live animal with water or aqueous detergent solution and thereafter apply to the animal while still alive, an aqueous mixture in which one or more surfactants or detergents are included in an aqueous microbiocidally-effective composition of this invention.

Type II Processing

As used anywhere herein including the claims, the term "carcass" denotes the body of the slaughtered four-legged slaughter animal at any stage of the processing operations used to convert the dead animal into meat. Thus the term "carcass" includes (i) the whole slaughtered animal body, (ii) the trunk of the body remaining after removal of the head and/or legs from the trunk of the animal, (iii) the severed head and the severed legs themselves, and (iv) the parts the trunk of the body after it has been split in two.

As used anywhere herein, including the claims, the term "during" denotes a period of time either (i) throughout the entire time a given operation is being conducted or (ii) at some portion or portions of the time a given operation is being conducted but not all of the time that such given operation is conducted. For example the phrase "during hide removal" means that some specified thing is done (i) at least throughout the entire time a hide removal operation is being carried out on a given carcass, or alternatively, (ii) for one or more time periods—but not throughout the entire time—a hide removal operation is being carried out on a given carcass. Note also that such hide removal operation (or other specified operation) need not be continuous in the sense, for example, that hide must be separated from the animal continuously from start to finish of the operation on a given carcass. Such removal can be continuous or non-continuous with pauses occurring during the overall operation (e.g., hide removal), and thus the specified thing is done either (i) at least throughout the entire time a given operation (e.g., hide removal) is being carried out on a given carcass including any pauses that occur in such operation, or alternatively, (ii) for one or more time periods—but not throughout the entire time—a given operation (e.g., hide removal) is being carried out on a given carcass including any pauses that occur in such operation.

As used anywhere herein, including the claims, the term "product solution" denotes the aqueous solution that results from mixing together at least water and one or more 1,3-dibromo-5,5-dialkylhydantoins. According to present theoretical concepts, 1,3-dibromo-5,5-dialkylhydantoins, to at least some extent, lose their original chemical structure when dissolved in an aqueous medium and the resultant composition, whatever it may be, is denoted herein as a "product solution" as it is formed from such specified components.

As used anywhere herein including the claims, the term "directly precedes" means that the specified thing (e.g., contacting a carcass with an aqueous microbiocidal composition) is done before the ensuing operation (e.g., hide or skin removal) has begun without any intervening operation being conducted except for transporting the carcass from the place where the specified thing was conducted to the place where the ensuing operation is to be done.

Pursuant to an embodiment of this invention, the external surfaces of a non-eviscerated carcass of at least one four-legged slaughter animal is contacted at least once with an aqueous microbiocidally-effective composition of this invention. This contacting can be effected by immersing the carcass in an aqueous microbiocidally-effective composition of this invention, by showering, spraying or misting the carcass with an aqueous microbiocidally-effective composition of this invention, or by using any other method of applying the aqueous microbiocidally-effective composition of this invention so that it comes into direct contact with the carcass before, during and/or after hide removal or after hair and/or bristle removal, but in each case prior to evisceration. Thus in the case of animal processing where the hide is removed followed by evisceration with or without an intermediate water wash, the contacting in this embodiment of the invention should take place before, during and/or after the hide removal stage but before the evisceration operation commences. In the case of animal processing where the hide is not removed before evisceration (e.g., where the carcass is subjected to singeing or shearing to remove hair and/or bristles, followed by evisceration, with or without an intermediate water wash), the contacting in this embodiment of the invention usually should take place after the singeing or shearing but before the evisceration operation commences. It is also possible to cause the contacting to occur during hair and/or bristle removal when the removal is conducted by a method other than singeing. In either such case (i.e., where hide is removed or where hide is not removed before evisceration), in a moving line of suspended spaced-apart carcasses, the contacting should be conducted such that the exposed surfaces of each carcass are wetted and remain wetted by the aqueous microbiocidal solution used pursuant to this invention for a period of at least 5 seconds, and preferably for a period of at least 30 seconds. Also in either such case the aqueous microbiocidally-effective composition of this invention can be preheated so that as applied to the carcass before evisceration the solution, spray or mist is at a temperature above room temperature but not higher than about 70° C., and preferably not higher than about 39° C. Since such heating does not materially diminish the biocidal activity of the aqueous microbiocidally-effective compositions of this invention, the ability to so heat such compositions ensures that customary processing line speeds in automated slaughterhouses will not be unduly compromised.

When applying an aqueous microbiocidally-effective composition of this invention to an animal carcass during hide removal it is convenient to employ either spraying or misting as the method of application. In this way the customary hide removal operation need not be materially altered in order to accommodate the application of the aqueous microbiocidally-effective composition of this invention to the carcass during hide removal.

In one preferred embodiment of the invention a series of spaced-apart suspended non-eviscerated animal carcasses is passed into a spray zone such as one or more cabinets or shower stall areas fitted with nozzles and/or spray heads that direct at least one spray or shower, preferably a plurality of sprays, of an aqueous microbiocidally-effective composition of this invention onto the surfaces of at least one carcass at a time as it passes through the spray zone. The coverage of the sprays should ensure that the surfaces of the suspended carcass are all exposed to, and come into contact with, the aqueous microbiocidally-effective composition of this invention. In this embodiment the non-eviscerated carcasses entering the spray zone will either have been skinned (i.e., the hide has been removed) or the hide or skin will remain intact but hair and/or bristles will have been removed from the carcass typically by singeing, shearing or other suitable hair and/or bristle removal technique, the choice between skinning and hair and/or bristle removal depending on the kind of animals being processed. For example, with cattle the hide will typically be removed prior to entry of the carcass into the spray zone for antimicrobial treatment of this invention with an aqueous microbiocidally-effective composition of this invention, whereas with swine, the carcass will typically be singed to burn off surface hair and/or bristles prior to entry of the carcass into the spray zone for such treatment. After the carcass exits the spray zone, typically the carcass will be washed with rinse water by any suitable technique such as dipping, spraying, submerging, etc., and then eviscerated, or will be subjected to evisceration as the next step in the processing without an intervening water wash.

Still another preferred embodiment of the invention involves applying an aqueous microbiocidally-effective composition of this invention to the animal carcass during evisceration. In order to minimize the possibility of interfering with the normal or conventional evisceration procedure, it is preferable to apply the aqueous microbiocidally-effective composition of this invention to the carcass as a mist or as a low-pressure fine spray during most if not all of the time the carcass is being eviscerated. Such misting or fine spraying ensures that the carcass and the entrails are both thoroughly wetted by the aqueous microbiocidally-effective composition of this invention without at the same time impairing the effectiveness of the operation. A particular advantage of this preferred embodiment is that microbial or bacterial contamination in the event of rupture of entrails is promptly combated by the presence and continuous application of the highly effective aqueous microbiocidal composition of this invention. As a consequence, contamination of ensuing carcasses by such microbial or bacterial contamination can be avoided without shutting the line down. As an adjunct to this preferred embodiment, the entrails after removal can be transported or conveyed to a washing zone where the entrails are submerged in a bath of an aqueous microbiocidally-effective composition of this invention for a period sufficient to ensure effective microbial and bacterial control.

A further embodiment of this invention is to conduct an inside-outside carcass washing of the eviscerated carcass prior to and/or during and/or after the carcass splitting operation. In conducting such inside-outside carcass washing pursuant to this invention, it is preferred to use a spray delivery system such as a probe or bayonet which pursuant to this invention applies a pressurized spray of the aqueous microbiocidally-effective composition of this invention to the interior cavity of the carcass and another spray delivery system such as a series of nozzles, which system applies the aqueous microbiocidally-effective composition of this invention to the exterior of the carcass. In particularly preferred embodiments of this invention the aqueous microbiocidally-effective composition of this invention applied by the spray delivery system to the interior cavity of the carcass has a higher concentration of microbiocide formed from 1,3-dibromo-5,5-dialkylhydantoin(s) than the concentration of the microbiocide formed from the 1,3-dibromo-5,5-dialkylhydantoin(s) in the water applied by the spray delivery system to the exterior the carcass. The 1,3-dibromo-5,5-dialkylhydantoin(s) used for forming the microbiocidal content in the water used for washing the interior cavity of the carcass and the 1,3-dibromo-5,5-dialkylhydantoin(s) used for forming the microbiocidal content of the water used for washing the exterior of the carcass can be, and usually will be, of the same chemical composition. However, 1,3-dibromo-5,5-dialkylhydantoin(s) of different chemical composition can be used for forming these respective aqueous microbiocidally-effective compositions of this invention for such inside-outside washing.

In another preferred embodiment of the invention a plurality of suspended eviscerated animal carcasses as they are being conveyed or otherwise transported into a cooling zone and/or after they have been received in a cooling zone are subjected while still warm (i.e., the carcasses have not lost all of the original body heat of the animal while alive) to at least one spray, shower, or mist of an aqueous microbiocidally-effective composition of this invention so that such composition comes into contact with both the inside and the outside of the carcass. When the suspended carcass is being transported toward the cooling zone, the spraying, showering, or misting of the traveling carcass can be effected within one or more suitable spray or misting cabinets or within one or more shower stalls or shower zones. Optionally, rinse water may be applied after application of the aqueous microbiocidally-effective composition of this invention. When the carcass is within the cooling zone, typically in a stationary fixed or rotatable position, such spraying, showering, or misting can be conducted continuously for a single suitable period of time, but preferably such sprays, showers, or mists can be periodically applied to the carcass. This preferred embodiment is particularly advantageous for use in the processing of cattle where carcasses are typically aged in a cooling zone for periods in the range of about 6 to about 16 hours. The application of such sprays, showers, or mists, especially if conducted periodically during the aging period, not only effectively prevents microbial development and growth, but keeps the meat from losing tenderness. In sharp contrast, application of a spray, shower, or mist of plain water during aging in a cooling zone in order to keep the meat from drying out and becoming tough, tends to result in an explosive growth of bacterial population.

Another feature of this invention is that the suspended eviscerated animal carcasses as they are being conveyed or otherwise transported into a cooling zone and/or after they have been received in a cooling zone can be sprayed, showered, or misted with an aqueous microbiocidally-effective composition of this invention that is itself at a low temperature of about 15° C. or below and preferably at about 10° C. or below, and more preferably at a temperature at about 7° C. or below, but in all cases above the freezing temperature of the microbiocidal solution. It can be seen therefore that in this operation the cold spray, shower, or mist used serves several functions. First of all, the cold spray, shower, or mist applied to these carcasses provides excellent microbial and/or bacterial control even though used at such low temperatures. Secondly the cold spray, shower, or mist when applied to the carcasses as they are being conveyed or otherwise transported into a cooling zone and/or shortly after they have been received in a cooling zone assists in chilling the carcasses. Thirdly, the cold spray, shower, or mist when applied to the carcasses that have already been chilled sufficiently so as to be at the desired low temperature, will not materially increase the temperature of the chilled carcasses. In all cases the coverage of the sprays, showers, or mists should ensure that the surfaces of the suspended carcass are exposed to the aqueous microbiocidally-effective composition of this invention.

Pursuant to another preferred embodiment of this invention, effective microbiocidal control in the processing of four-legged slaughter animals, especially cattle or swine, is brought about by use of an aqueous microbiocidally-effective composition of this invention in at least two of three important animal processing stages or stations, whereby without materially affecting productivity, more effective microbiocidal control is achieved as compared to use of the hypochlorite or other chlorine-derived microbiocides.

More particularly, pursuant to this preferred embodiment of this invention water treated with at least one 1,3-dibromo-5,5-dialkylhydantoin to form an aqueous microbiocidally-effective composition of this invention is brought into contact with the carcass of a four-legged slaughter animal during at least two of the following three operations: (1) before, during and/or after hide removal or before and/or after hair and/or bristle removal, and in some cases during hair and/or bristle removal by methods other than singeing, (2) during evisceration, and (3) immediately prior to and/or during chilling Methods for carrying out each of these three operations have been described hereinabove.

In a particularly preferred embodiment, an aqueous microbiocidally-effective composition of this invention is utilized in at least two, preferably at least three, more preferably at least four, and most preferably in at least five of the following operations for a state-of-the-art slaughter house in the processing of cattle: (1) hide removal, (2) disinfection between hide removal and prior to evisceration, (3) evisceration, (4) carcass splitting, (5) final wash, and (6) chill. Operations other than (2) are typically carried out in state-of-the-art slaughterhouses in the processing of cattle, but of course without using an aqueous microbiocidally-effective composition of this invention in any operation. Operation (2) is an operation believed to be unique to this invention. Methods for carrying out operations (1), (2), (3), (4), and (6) in accordance with this invention have been described hereinabove. In operation (5), i.e., the final wash operation, any conventional way of carrying out such an operation can be used pursuant to this invention simply by including in some or all of the wash water an aqueous microbiocidally-effective composition of this invention.

In another particularly preferred embodiment, an aqueous microbiocidally-effective composition of this invention is utilized in at least two, preferably at least three, and most preferably in all four of the following operations: utilized in a state-of-the-art slaughter house in the processing of swine: (1) disinfection between hide removal and prior to evisceration, (2) evisceration, (3) splitting, and (4) chill. Operations other than (1) are typically carried out in state-of-the-art slaughterhouses in the processing of cattle, but of course without using an aqueous microbiocidally-effective composition of this invention in any operation. Operation (1) is an operation believed to be unique to this invention. Methods for carrying out operations (1), (2), (3), and (4) in accordance with this invention have been described hereinabove.

In conducting spraying operations pursuant to this invention in one or more of the various stages or locations in an animal carcass processing line, the nozzles used for applying the aqueous microbiocidally-effective composition of this invention to the animal carcass can be fixed or articulating nozzles. In addition, during spraying, showering or misting steps used in the practice of this invention, rotary brushes or other ways of increasing contact between the aqueous microbiocidally-effective composition of this invention and the carcass, such as use of ultrasonic energy, can be used. Thereafter the carcass can be rinsed with clear water, if deemed necessary or desirable. Such rinsing water can be fresh or recirculated water, or a combination of both. The recirculated water should be effectively purged of residual impurities from prior usage.

It is possible pursuant to a further embodiment of this invention to minimize the amount of waste water generated in carrying out various embodiments of this invention. For example, in a system wherein a plurality of individual suspended carcasses are transported through the processing line having various processing stations, at least one given station is provided with at least one suitably-positioned motion sensor or detector operatively associated with apparatus to start and stop the flow of aqueous microbiocidally-effective composition of this invention to that station of the line. When the sensor detects that a carcass is entering a specified zone in that station where the spray, shower, or mist is to be applied to the carcass, the sensor sends a signal to the start-stop apparatus which turns on the flow of aqueous microbiocidally-effective composition of this invention. This flow can be maintained and then shut off by the system in various ways. One way is for the flow to last for a specified time period coordinated with the travel rate of carcasses through the line at that station so that after a sufficient time period during which a predetermined amount of spray, shower, or mist has been applied to the carcass, the flow of spray, shower, or mist is automatically stopped.

Another way is to automatically cut off the flow after a predetermined the volume of liquid flow has been sent to the spray, shower, or misting devices. Still another way is for another motion sensor or detector to sense when the carcass has advanced to a second position in that station and thereupon to signal the start-stop apparatus to turn off the flow. The motion sensors or detectors can be positioned to sense the presence of the carcass itself. Alternatively they can be positioned to sense the presence of a suitable portion of the carcass transporting system such as the traveling carrier for the carcass suspension mechanism, or the carcass suspension mechanism or a portion thereof such as the wire, cable, chain, shackle, or hook that is holding the suspended carcass.

Suitable motion sensing or detection devices known in the art can be adapted for use in the above waste water minimization embodiment of this invention. The so-called electric eye that senses the presence of a person entering an elevator and causes the elevator doors to remain open or to retract the doors serves as a commonly encountered sensing device. Various other devices are known. See for example U.S. Pat. No. 6,623,348.

In the practice of this invention in Type II operations, the aqueous microbiocidally-effective composition of this invention can be applied before and/or during making incisions in the carcass for the purpose of inspection as well as for evisceration.

Type III Processing

This type of processing pursuant to this invention comprises contacting raw meat products and/or processed meat products derived from the slaughtered animal(s), with an aqueous microbiocidal composition formed by mixing at least one 1,3-dibromo-5,5-dialkylhydantoin with an aqueous medium to form an aqueous microbiocidally-effective composition. This contacting should occur at one or more suitable stages before, during and/or after the formation or preparation of such raw meat and/or meat products. The methods of applying an aqueous microbiocidally-effective composition of this invention to the raw meat and/or meat products are much the same as described above. Thus spraying, to dipping, bathing, showering or like operations can be used. Also, in small slaughter houses or meat packing plants, hand-held sponges or washing cloths may be used for applying the aqueous microbiocidally-effective composition of this invention. The raw meat products and/or processed meat products or precursors thereof, can be conveyed by automated conveying equipment such as conveyor belts on which such products or precursors are carried and transported, or moving tracks, belts, or cables by which such products or precursors are suspended, carried, and transported.

The raw meat that can be contacted with an aqueous microbiocidally-effective composition of this invention can be in any form typically derived from the animal carcass. Non-limiting examples of such raw meat products include (a) meat cuts as for example steaks, chops, rib sections, meat roast cuts, hams, loins, bacon, and other similar cuts, (b) animal organs such as liver, kidney, tripe, chitlins, tongue, and other organs or organ parts, and (c) ground raw meat such as ground beef, ground pork, raw meat sausages, and the like. Non-limiting examples of processed meat products that can be contacted with an aqueous microbiocidally-effective composition of this invention include ready-to-eat deli products, sausages, frankfurters, sliced meats, jerky, and/or other processed meat products.

Preferred raw meat products to which an aqueous microbiocidally-effective composition of this invention is applied include red meat, red meat parts, white meat, and white meat parts. Most preferred is the application an aqueous microbiocidally-effective composition of this invention to raw red meat (beef) from cattle or to raw white meat (pork) from swine.

Figure 1:
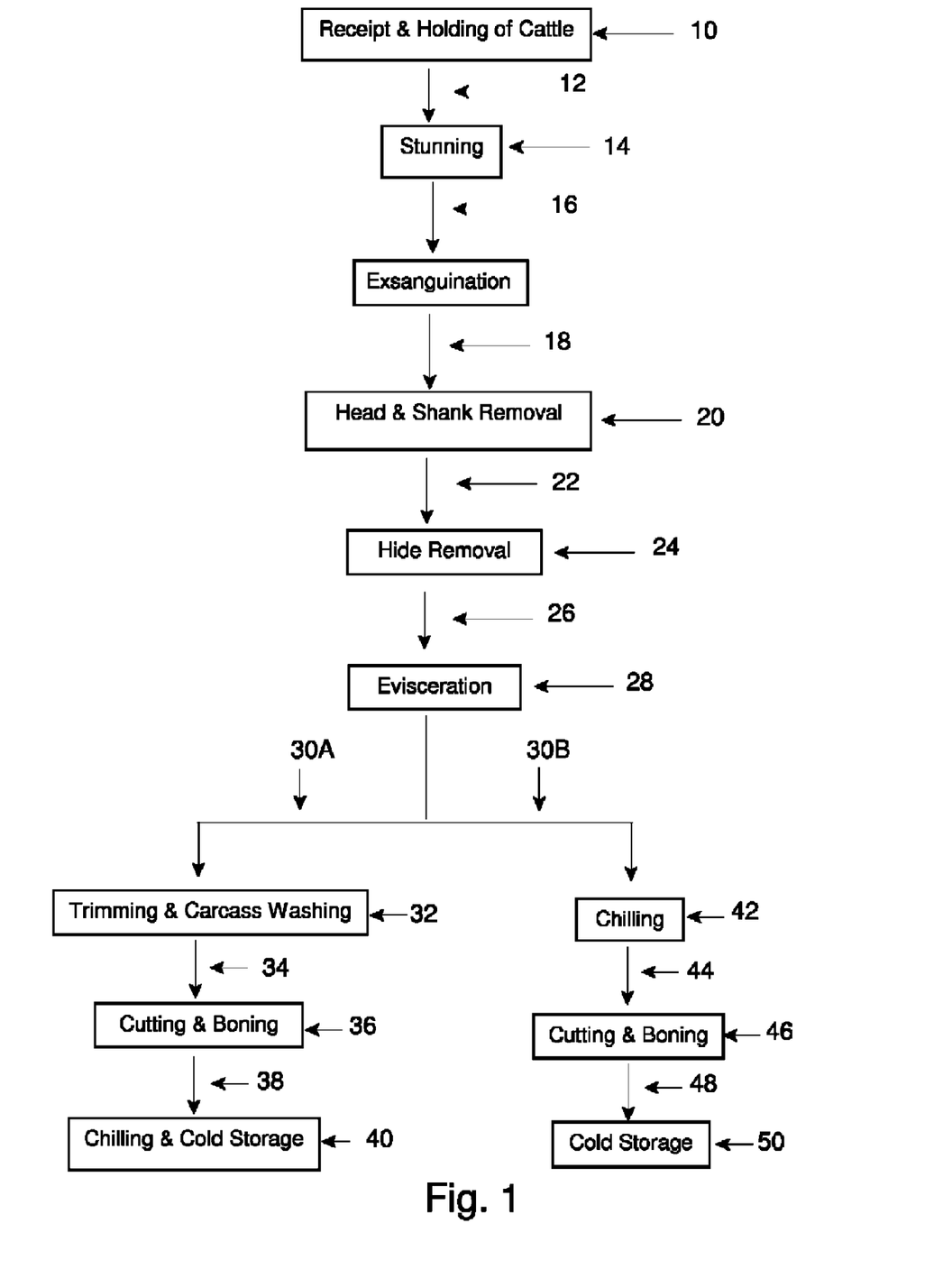
FIG. 1 is a block diagram illustrating typical stages during the processing of cattle at which, pursuant to this invention, cattle and/or cattle carcasses can be contacted with the aqueous microbiocidally-effective compositions used pursuant to this invention.
Figure 2:
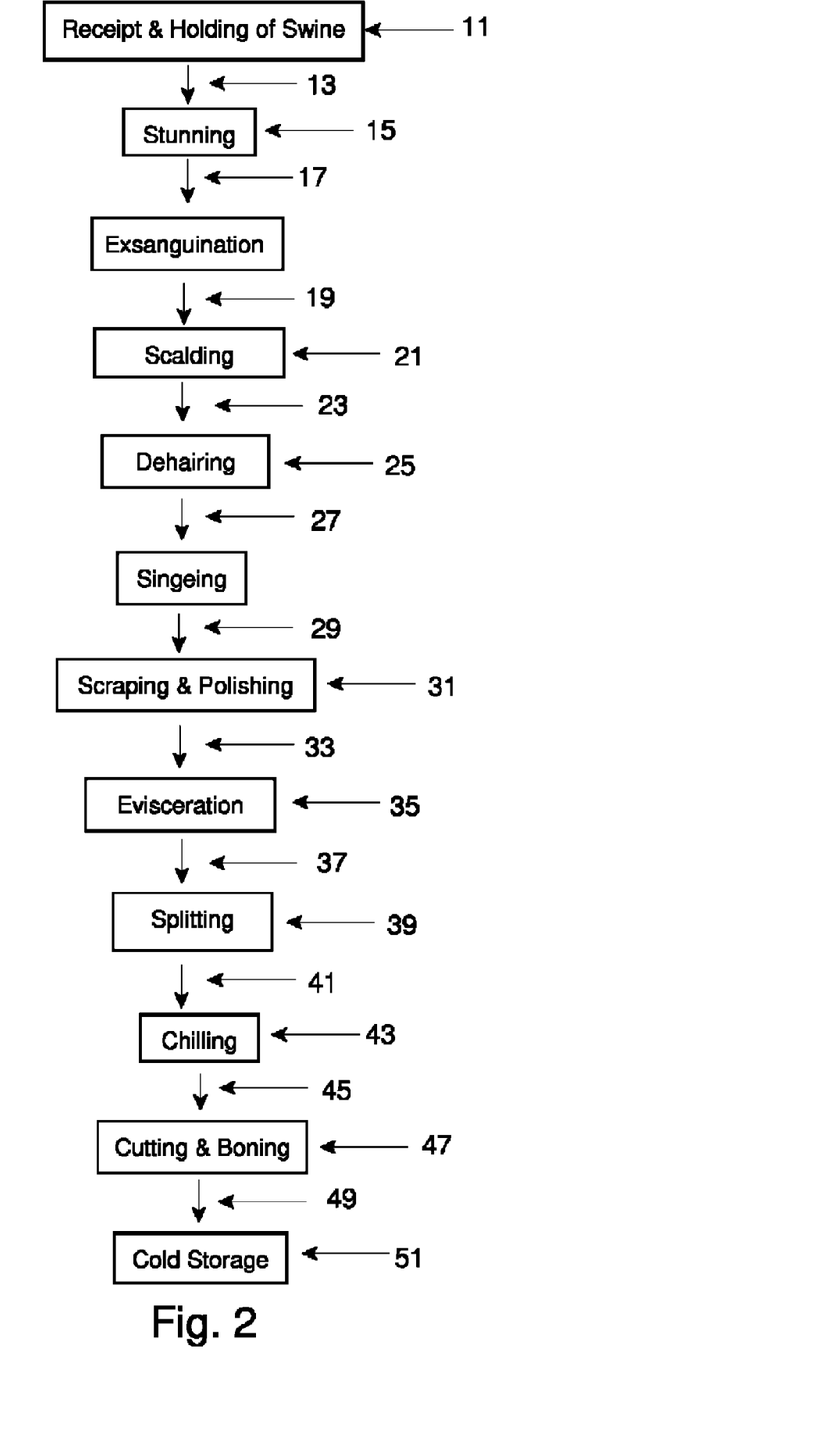
FIG. 2 is a block diagram illustrating typical stages during the processing of swine at which, pursuant to this invention, swine and/or swine carcasses can be contacted with the aqueous microbiocidally-effective compositions used pursuant to this invention.

In Type III processing, the aqueous microbiocidally-effective composition of this invention used will be a composition formed by mixing water and at least one 1,3-dibromo-5,5-dialkylhydantoin microbiocidal agent in an amount in the range of about 0.5 to about 400 ppm (wt/wt). The particular concentration of the one or more 1,3-dibromo-5,5-dialkylhydantoins used in forming such compositions, will vary depending upon the particular raw meat product and/or processed meat product being produced. In many cases such as in the treatment of raw meat cuts and ground or sliced meat products, the concentration of the 1,3-dibromo-5,5-dialkylhydantoin microbiocidal agent used in forming the composition used, will be at the lower end of this range for example in the range of about 0.5 to about 100 ppm (wt/wt) and in some case as low as in the range of about 0.5 to about 50 ppm (wt/wt). In other words, in many cases the bromine residual in the compositions formed from water and one or more 1,3-dibromo-5,5-dialkylhydantoins will be in the range of about 0.5 to about 100 ppm (wt/wt) as free bromine, and in some cases will be as low as in the range of about 0.5 to about 50 ppm (wt/wt) as free bromine Reference to the Drawings The block diagrams of FIGS. 1 and 2 serve to illustrate, but not limit, the invention as applied respectively to cattle and swine. As seen from the cattle processing stages depicted in FIG. 1, and the swine processing stages depicted in FIG. 2, there are a series of stages which typically can be used in a large state of the art slaughter house or meat packing plant. It is to be understood and appreciated that some of the stages depicted can be combined with one or more other stages and that some of the stages may be eliminated. Moreover, some of the stages depicted can be carried out in a different sequence from that depicted. Nevertheless, FIGS. 1 and 2 are deemed to illustrate at least some of the ways by which the present invention can be practiced with respect to live animals and their carcasses after slaughter. To a limited extent the processing of raw meat products pursuant to this invention can also be appreciated from these drawings.

Turning now to FIG. 1, the numerals represent typical stages at which pursuant to this invention, the live animal, carcass, or parts thereof can be contacted with an aqueous microbiocidally-effective composition of this invention. Thus, such contacting can be carried out as at 10 during the receipt and holding of cattle, and/or during travel of the live animal to stunning as at 12, and/or during stunning as at 14, and/or during transport of the stunned live animal to exsanguination as at 16. Such contacting can also be carried out at any one or more of the following stages: before head and shank removal as at 18, and/or during head and shank removal as at 20, and/or before hide removal as at 22, and/or during hide removal as at 24, and/or before eviseration as at 26, and/or during eviseration as at 28. At this point of the processing, one of two commonly-used approaches can be utilized. In one approach, the contacting pursuant to this invention can occur at one or more of the following stages: before trimming and carcass washing as at 30A, and/or during trimming and carcass washing as at 32, and/or before cutting and boning as at 34, and/or during cutting and boning as at 36, and/or before chilling and cold storage as at 38, and/or during chilling and cold storage as at 40. In the second approach, the contacting pursuant to this invention can occur at one or more of the following stages: before chilling as at 30B, and/or during chilling as at 42, and/or before cutting and boning as at 44, and/or to during cutting and boning as at 46, and/or before cold storage as at 48, and/or during cold storage as at 50. It will be noted that pursuant to this invention the contacting as depicted in FIG. 1 can occur at any one or more of the depicted stages except for during exsanguination. This represents a preference inasmuch as the contacting during exsanguination would tend to dilute the blood released from the animal. However, pursuant to this invention, it is possible to carry out the contacting during exsanguination.

FIG. 2 illustrates in a manner similar to FIG. 1 stages during the processing of swine at which the live animal, carcass, or parts thereof can be contacted with an aqueous microbiocidally-effective composition of this invention. Thus, such contacting can be carried out as at 11 during the receipt and holding of swine, and/or during travel of the live animal to stunning as at 13, and/or during stunning as at 15, and/or during transport of the stunned live animal to exsanguination as at 17. Such contacting can also be carried out at any one or more of the following stages: before scalding as at 19, and/or during scalding as at 21, and/or before dehairing as at 23, and/or during dehairing as at 25, and/or before singeing as at 27, and/or before scraping and polishing as at 29, and/or during scraping and polishing as at 31, and/or before eviseration as at 33, and/or during eviseration as at 35, and/or before carcass splitting as at 37, and/or during carcass splitting as at 39, and/or before carcass chilling as at 41, and/or during carcass chilling as at 43, and/or before cutting and boning as at 45, and/or during cutting and boning as at 47, and/or before cold storage as at 49, and/or during cold storage as at 51. It will be seen that pursuant to this invention the contacting as depicted in FIG. 2 can occur at any one or more of the depicted stages except for during exsanguination and during singeing. The avoidance of contacting during exsanguination represents a preference inasmuch as the contacting during exsanguination would tend to dilute the blood released from the animal. However, pursuant to this invention, it is possible to carry out the contacting during exsanguination. In addition, the avoidance of contacting during singeing represents another preference as the application of an aqueous solution to the carcass during singeing would not be conducive to the ordinary conditions used for conducting a singeing operation. However, if singeing conditions can be devised so that the presence of an aqueous solution would not unduly interfere with such a singeing operation, the contacting pursuant to this invention can, under such circumstances, be utilized.

Other Considerations

As seen from the above, one or more aqueous microbiocidally-effective compositions of this invention are used to effectively control microbial and bacterial contamination of live four-legged slaughter animals, four-legged slaughter animal carcasses, and/or raw meat products and/or processed meat products derived from four-legged slaughter animal carcasses in one or more specified locations in an animal slaughter house or meat packing plant. Such aqueous microbiocidally-effective compositions of this invention are formed by dissolving one or more 1,3-dibromo-5,5-dialkylhydantoins in water. Preferred are 1,3-dibromo-5,5-dialkylhydantoins in which one of the alkyl groups is a methyl group and the other alkyl group contains in the range of 1 to about 4 carbon atoms. Thus these preferred biocides comprise 1,3-dibromo-5,5-dimethylhydantoin, 1,3-dibromo-5-ethyl-5-methylhy-dantoin, 1,3-dibromo-5-n-propyl-5-methylhydantoin, 1,3-dibromo-5-isopropyl-5-methylhy-dantoin, 1,3-dibromo-5-n-butyl-5-methylhydantoin, 1,3-dibromo-5-isobutyl-5-methylhydantoin, 1,3-dibromo-5-sec-butyl-5-methylhydantoin, 1,3-dibromo-5-tert-butyl-5-methylhydantoin, and mixtures of any two or more of them. Of these biocidal agents, 1,3-dibromo-5-isobutyl-5-methylhydantoin, 1,3-dibromo-5-n-propyl-5-methylhydantoin, and 1,3-dibromo-5-ethyl-5-methylhydantoin are, respectively, preferred, more preferred, and even more preferred members of this group from the cost effectiveness standpoint. Of the mixtures of the foregoing biocides that can be used pursuant to this invention, it is preferred to use 1,3-dibromo-5,5-dimethylhydantoin as one of the components, with a mixture of 1,3-dibromo-5,5-dimethylhydantoin and 1,3-dibromo-5-ethyl-5-methylhydantoin being particularly preferred. The most preferred member of this group of microbiocides is 1,3-dibromo-5,5-dimethylhydantoin. This compound is available in the marketplace under the trade designations XtraBrom®111 microbiocide and XtraBrom®111T microbiocide (Albemarle Corporation). When a mixture of two or more of the foregoing 1,3-dibromo-5,5-dialkylhydantoin biocides is used pursuant to this invention, the individual biocides of the mixture can be in any proportions relative to each other. Minor proportions of mono-N-bromo-5,5-dialkylhydantoin(s) can be present along with the 1,3-dibromo-5,5-dialkylhydantoin(s) but such compositions are not preferred.

Methods for producing 1,3-dibromo-5,5-dialkylhydantoins are known and reported in the literature. An especially preferred method is described in WO 01/53270 published 26 Jul. 2001.

The 1,3-dibromo-5,5-dialkylhydantoin(s) used pursuant to this invention can be blended directly in the water to be used in the various stages or locations referred to herein. For this purpose suitable dispensing devices can be employed that meter into water flowing through the device suitable amounts of the 1,3-dibromo-5,5-dialkylhydantoin(s) microbiocides. Alternatively, predetermined quantities of micronized 1,3-dibromo-5,5-dialkylhydantoin(s) may be added to water in amounts in excess of the final use level, and the resultant concentrate can be further diluted, preferably with agitation, with one or more different amounts of water to form one or more treated water compositions to be used in the respective stages of the process.

Other additives can be used in conjunction with the 1,3-dibromo-5,5-dialkylhydantoin(s) provided the other additive or additives are non-toxic, are compatible with aqueous microbiocidal solutions formed by dissolving the 1,3-dibromo-5,5-dialkylhydantoin(s) in water to form the treated water used pursuant to this invention, and do not otherwise detract from the microbiocidal effectiveness of the treated water in any appreciable manner. By "in conjunction with" is meant that in most cases the other additive component(s) are fed separately into the water being used; e.g., the other additives, if susceptible to oxidation by common oxidants, are not mixed directly with the undissolved 1,3-dibromo-5,5-dialkylhydantoin(s). In general, additives which are compatible with aqueous hypohalite bleach solutions such as certain radical scavengers, chelating agents, pH buffering agents, surfactants, detergents, and polymers described in detail, for example, in U.S. Pat. No. 6,506,718 or other published literature on the subject may be used, if desired. It is also possible to use one or more wetting agents, hydrotropes, thickeners, defoaming agents, and similar functional additives that meet the above criteria. If used, the amount of each suitable selected additive to be used in conjunction with the 1,3-dibromo-5,5-dialkylhydantoin(s) should be sufficient to provide the property for which it is employed. Recommendations from manufacturers of such other additives are useful as guidelines in this respect.

Preferably the one 1,3-dibromo-5,5-dialkylhydantoin or the more than one 1,3-dibromo-5,5-dialkylhydantoin is the sole originating source of microbiocidal activity in the aqueous medium treated therewith. However this invention includes use in the above operations of aqueous media treated with (A) at least one 1,3-dibromo-5,5-dialkylhydantoin and (B) at least one other microbiocidal agent which produce a suitably to stable compatible aqueous microbiocidal composition. In other words, the solution products of (A) and (B) should be compatible with each other in the aqueous medium when present in the amounts and proportions that provide an aqueous microbiocidal composition.

The contacting or washing operations when used pursuant to this invention ensure that pathogens such as species of *Listeria, Escherichia, Salmonella, Campylobacter*, and others, are effectively controlled, if not essentially eliminated from the meat product. Moreover, in large scale four-legged slaughter animal processing lines where high throughput is essential, the microbiocide of this invention used in these stages or stations is so effective that it is not necessary to slow down the line to give the microbiocide time to act. Thus the processing lines can be operated at conventional speeds, if not at increased speeds. Further, the waters used in the respective stages or stations can each be treated with suitable microbiocidal quantities of a given 1,3-dibromo-5,5-dialkylhydantoin microbiocidal agent, and thus it is possible to use only one such agent throughout the plant, thus simplifying the purchasing, storage and inventory aspects of the plant operation. Indeed it is possible to use water containing the same microbiocidal concentration (i.e., the same bromine residual resulting from dissolving in water a given amount one or more 1,3-dibromo-5,5-dialkylhydantoins) in the water going to each of multiple stages or locations in the embodiments of this invention where an aqueous microbiocidally-effective composition of this invention is used at more than one stage or location in a processing line.

In the practice of various embodiments of this invention, aqueous washing solutions can be used before and, especially after, applying the aqueous microbiocidally-effective composition of this invention to the live animal, animal carcass, the raw meat product, and/or the processed meat product. Such aqueous washing solutions can contain any of a variety of useful additional components such as for example sodium chloride, sodium hydroxide, potassium sorbate, sodium bisulfate, lactic acid, sodium metasilicate, acidified sodium chlorite, polypeptide antibiotic such as nisin, or other known components serving similar functions.

The animal carcass, raw meat product, and/or the processed meat product after contacting with an aqueous microbiocidally-effective composition of this invention and optionally a subsequent washing solution, can be subjected to additional sanitizing operations. Thus, in accordance with another embodiment of this invention, there is provided a method of processing the carcass of a four-legged slaughter animal and/or raw meat product derived from said carcass, and/or processed meat product derived from said carcass, which method comprises (a) contacting said carcass, raw meat product derived from said carcass, and/or processed meat product derived from said carcass at least once with a microbiocidal solution formed from mixing together at least (i) water and (ii) at least one 1,3-dibromo-5,5-dialkylhydantoin, and (b) subjecting the resultant carcass, raw meat product derived from said carcass, and/or processed meat product derived from said carcass to at least one decontamination process selected from ionizing radiation, UV radiation, microwaves, pulsed light, electric fields, hydrostatic pressure, sonication, infra-red radiation, ozonization, and ozone washing. Steps (a) and (b) can be carried out in any sequence and/or concurrently.

Suitable methods for determining "bromine residual" are known and reported in the literature. See for example, *Standard Methods For the Examination of Water and Wastewater*, 18th Edition, 1992, from American Public Health Association, 1015 Fifteenth Street, NW, Washington, D.C. 20005 (ISBN 0-87553-207-1), pages 4-36 and 4-37; *Hach Water Analysis Handbook*, Third Edition, 1997, by Hach Company, Loveland Colo., especially pages 1206 and 1207; and *Handbook of Industrial Water Conditioning*, 7th edition, Betz Laboratories, Inc., Trevose, Pa. 19047 (Library of Congress Catalog Card Number: 76-27257), 1976, pages 24-29. While these references typically refer to "chlorine residual", the same techniques are used for determining "bromine residual", by taking into account the higher atomic weight of bromine as compared to chlorine.

The term "bromine residual" refers to the amount of bromine species present in the treated water available for disinfection. Residuals can be determined as either "free" or "total" depending upon the analytical test method employed. In the present case, the numerical values for bromine residual have been given herein on a free bromine basis. Such values can be monitored by use of the analytical procedure for "free chlorine" given below. However if desired, the bromine residual could be monitored on a "total bromine" basis by using the analytical procedure for "total chlorine" given below. In either case the numerical values obtained are in terms of chlorine and thus such values are multiplied by 2.25 to obtain the corresponding bromine values. Typically the values on a "total bromine" basis on a given sample will be higher than the values on a "free bromine" basis on the same given sample. The important point to understand is that this invention relates to the bromine residual that is actually present in the treated aqueous medium whether the to value is determined by use of the free chlorine test procedure or the total chlorine test procedure, but use of the free chlorine test procedure is recommended.

A standard test for determination of low levels of active halogen is known as the DPD test and is based on classical test procedures devised by Palin in 1974. See A. T. Palin, "Analytical Control of Water Disinfection With Special Reference to Differential DPD Methods For Chlorine, Chlorine Dioxide, Bromine, Iodine and Ozone", *J. Inst. Water Eng.*, 1974, 28, 139. While there are various modernized versions of the Palin procedures, the recommended version of the test is fully described in *Hach Water Analysis Handbook*, 3rd edition, copyright 1997. The procedure for "total chlorine" (i.e., active chlorine) is identified in that publication as Method 8167 appearing on page 379, Briefly, the "total chlorine" test involves introducing to the dilute water sample containing active halogen, a powder comprising DPD indicator powder, (i.e., N,N'-diethyldiphenylenediamine, KI, and a buffer). The active halogen species present react(s) with KI to yield iodine species which turn the DPD indicator to red/pink The intensity of the coloration depends upon the concentration of "total chlorine" species (i.e., active chlorine") present in the sample. This intensity is measured by a colorimeter calibrated to transform the intensity reading into a "total chlorine" value in terms of mg/L $Cl_2$. If the active halogen present is active bromine, the result in terms of mg/L $Cl_2$ is multiplied by 2.25 to express the result in terms of mg/L $Br_2$ of active bromine.

In greater detail, the DPD test procedure is as follows:
1. To determine the amount of species present in the water which respond to the "total chlorine" test, the water sample should be analyzed within a few minutes of being taken, and preferably immediately upon being taken.
2. Hach Method 8167 for testing the amount of species present in the water sample which respond to the "total chlorine" test involves use of the Hach Model DR 2010 colorimeter. The stored program number for chlorine determinations is recalled by keying in 80 on the keyboard, followed by setting the absorbance wavelength to 530 nm by rotating the dial on the side of the instrument. Two identical sample cells are filled to the 10 mL mark with the water under investigation. One of the cells is arbitrarily chosen to be the blank. To the second cell, the contents of a DPD Total Chlorine Powder Pillow are added. This is shaken for 10-20 seconds to mix, as the development of a pink-red color indicates the presence of species in the water which respond positively to the DPD "total chlorine" test reagent. On the keypad, the SHIFT TIMER keys are depressed to commence a three minute reaction time. After three minutes the instrument beeps to signal the reaction is complete. The blank sample cell is admitted to the sample compartment of the Hach Model DR 2010, and the shield is closed to prevent stray light effects. Then the ZERO key is depressed. After a few seconds, the display registers 0.00 mg/L $Cl_2$. Then, the blank sample cell used to zero the instrument is removed from the cell compartment of the Hach Model DR 2010 and replaced with the test sample to which the DPD "total chlorine" test reagent was added. The light shield is then closed as was done for the blank, and the READ key is depressed. The result, in mg/L $Cl_2$ is shown on the display within a few seconds. This is the "total chlorine" level of the water sample under investigation. It is to be noted that the test sample may need to be diluted with halogen demand free water in order for the chlorine measurement to be within the measuring range of the instrument. This dilution will need to be taken into account to determine the actual chlorine level of the sample.
3. One method for measuring free chlorine is the Hach Method 8021. This tests for the amount of species present in the water sample which respond to the "free chlorine" test. This test involves the use of the Hach Model DR 2010 colorimeter. The stored program number for chlorine determinations is recalled by keying in 80 on the keyboard, followed by setting the absorbance wavelength to 530 nm by rotating the dial on the side of the instrument. Two identical sample cells are filled to the 10 mL mark with the water under investigation. One of the cells is arbitrarily chosen to be the blank. The blank sample cell is admitted to the sample compartment of the Hach Model DR 2010, and the shield is closed to prevent stray light effects. Then the ZERO key is depressed. After a few seconds, the display registers 0.00 mg/L $Cl_2$. Then, the blank sample cell used to zero the instrument is removed from the cell compartment of the Hach Model DR 2010. To the second cell, the contents of a DPD Free Chlorine Powder Pillow are added. This is shaken for 10-20 seconds to mix, as the development of a pink-red color indicates the presence of species in the water which respond positively to the DPD "free chlorine" test reagent Immediately (within one minute of reagent addition) place the prepared sample into the cell holder. The light shield is then closed as was done for the blank, and the READ key is depressed. The result, in mg/L $Cl_2$ is shown on the display within a few seconds. This is the "free chlorine" level of the water sample under investigation. It is to be noted that the test sample may need to be diluted with halogen demand free water in order for the chlorine measurement to be within the measuring range of the instrument. The dilution will need to be taken into account when determining the chlorine level of the sample.

One end result achievable by the practice of this invention is that highly effective minimization of microbiological contamination within the slaughterhouse or meat packing plant can be achieved by minimizing the extent to which microbacterial contamination is brought into the slaughterhouse or meat packing plant by the live animals themselves. Another end result is that highly effective minimization of microbiological contamination of the carcass and meat product can be achieved at each of the stages or locations of the animal carcass processing line. In addition, the invention enables the provision of a meat product in which the taste, sensory quality, appearance, and wholesomeness of the product should not be adversely affected in any material manner by the microbiocidal operations conducted pursuant to this invention. And when properly conducted, this invention makes possible achievement of significantly higher microbial control than achieved with comparable levels of previously known microbiocides for use in treatment of animal carcasses, such as hypochlorite in water.

As noted above it is vitally important that the method used for effectively controlling microbial and/or bacterial contamination on animal carcasses and parts thereof, not cause any noticeable degradation in the quality or properties of the meat from the carcasses, especially in the appearance and taste of the meat. The following Example demonstrates the ability of this invention to avoid any noticeable degradation in the quality or properties of the meat from carcasses of four-legged slaughter animals, especially in the appearance and taste of the meat.

Example

A study was conducted in which individual samples of raw meat were directly contacted individually with a test substance to determine the effect each such substance had on the quality of the meat. The raw meat used was top round beef. The test materials were: (a) household bleach (commercially available hypochlorite bleach solution); (b) water-diluted household bleach containing 50 ppm as chlorine bleach; (c) 2% aqueous lactic acid solution; and pursuant to this invention, (d) 100 ppm as bromine of 1,3-dibromo-5,5-dimethylhydantoin (DBDMH). Individual samples of beef (approximately 30 grams each) were placed in 80 mm×40 mm crystallization dishes. Each such sample was exposed to 30.0 grams of one of the respective test materials for a period of 5 minutes. The beef samples were not totally immersed in their respective test material. Instead, the quantities used were such that one side of each beef sample was not contacted by its test material. After the 5-minute exposure, the area exposed to the test material was rinsed with deionized water and patted dry with a paper towel. After several minutes the color of the treated meat was compared to an untreated piece of the meat, and also to the samples of meat treated with another of the test materials. The beef sample treated with commercially-available household bleach solution was very dark, and the beef sample treated with water-diluted commercially-available household bleach solution was slightly darker than the untreated meat. The lactic acid-treated meat sample appeared to be very similar in color to the untreated beef. Surprisingly, the sample of beef treated with the aqueous microbiocidal composition used pursuant to this invention formed from DBDMH and water was slightly lighter in appearance than the untreated beef. If one considered the oxidation potentials of the test materials used, the following effect would be expected:

Household bleach>dilute bleach>DBDMH

Also, based on the bleach results it would be expected that the meat treated with DBDMH would darken in appearance rather than become slightly lighter in appearance.

Compounds referred to by chemical name or formula anywhere in this document, whether referred to in the singular or plural, are identified as they exist prior to coming into contact with another substance referred to by chemical name or chemical type (e.g., another component, a solvent, or etc.). It matters not what chemical changes, if any, take place in the resulting mixture or solution, as such changes are the natural result of bringing the specified substances together under the conditions called for pursuant to this disclosure. As an example, the phase "water treated with at least one 1,3-dihalo-5,5-dialkylhydantoin" and phrases of similar import signify that just before being brought into contact with an aqueous medium such as water, the at least one 1,3-dihalo-5,5-dialkylhydantoin referred to was the specified 1,3-dihalo-5,5-dialkylhydantoin. The phrase thus is not intended to suggest or imply that the chemical exists unchanged in the water. The transformations that take place are the natural result of bringing these to substances together, and thus need no further elaboration.

Also, even though the claims may refer to substances in the present tense (e.g., "comprises", "is", etc.), the reference is to the substance as it exists at the time just before it is first contacted, blended or mixed with one or more other substances in accordance with the present disclosure.

Except as may be expressly otherwise indicated, the article "a" or "an" if and as used herein is not intended to limit, and should not be construed as limiting, the description or a claim to a single element to which the article refers. Rather, the article "a" or "an" if and as used herein is intended to cover one or more such elements, unless the text expressly indicates otherwise.

All documents referred to herein are incorporated herein by reference in Coto as if fully st forth in this document.

This invention is susceptible to considerable variation within the spirit and scope of the appended claims.

That which is claimed is:

1. A method of processing a four-legged slaughter animal for consumption as meat and/or meat product(s), said method comprising:
   A) contacting a carcass of said animal, after exsanguination, with a microbiocidal solution formed from mixing together at least (i) water and (ii) at least one 1,3-dibromo-5,5-dialkylhydantoin; or
   B) contacting at least one raw meat product and/or at least one processed meat product derived from said carcass at least once with a microbiocidal solution formed from mixing together at least (i) water and (ii) at least one 1,3-dibromo-5,5-dialkylhydantoin; or
   C) conducting A) and B); or
   D) contacting exterior surfaces of the live animal at least once with a microbiocidal solution formed from mixing together at least (i) water and (ii) at least one 1,3-dibromo-5,5-dialkylhydantoin, said contacting occurring at least once when the animal is en route to being slaughtered but before it is killed by exsanguination; and also conducting A) or B) or C).

2. A method as in claim 1 wherein A) is conducted.

3. A method as in claim 2 wherein (i) said contacting at least is conducted before, during, and/or after hide or hair or skin removal from the carcass of an animal from which hide or hair or skin is removed during processing, or (ii) said contacting at least is conducted before and/or after bristle removal from the carcass of an animal from which bristles are removed during processing, or (iii) said contacting at least is conducted during bristle removal by a method other than singeing from the carcass of an animal from which bristles are removed during processing.

4. A method as in claim 2 wherein said animal is selected from steers, heifers, cows, calves, and bulls, and said contacting at least is conducted:
   (i) one or more times prior, during and/or after head and/or shank removal; or
   (ii) during carcass splitting and/or one or more times after carcass splitting; or
   (iii) during final wash and/or one or more times after final wash; or
   (iv) one or more times during chilling and/or one or more times after chilling; or
   (v) one or more times during carcass cutting and boning and/or one or more times after carcass cutting and boning; or
   (vi) one or more times during hot boning.

5. A method as in claim 2 wherein said animal is selected from hogs, sows, gilts, barrows, boars and pigs, and said contacting at least is conducted
   (i) prior to scalding the carcass; or
   (ii) during and/or one or more times after dehairing and/or singeing the carcass; or
   (iii) during and/or one or more times after scraping and/or polishing said carcass; or
   (iv) during and/or one or more times after evisceration; or
   (v) during carcass splitting; or
   (vi) one or more times during chilling and/or one or more times after chilling; or
   (vii) one or more times during cutting and boning said carcass; or
   (viii) one or more times during cold storage.

6. A method as in claim 1 wherein B) is conducted.

7. A method as in claim 6 wherein the microbiocidal solution used in said contacting is formed from water and a biocidally effective amount of said 1,3-dibromo-5,5-dialkylhydantoin in the range of about 0.5 to about 400 parts by weight of 1,3-di-bromo-5,5-dialkylhydantoin per million parts by weight of water.

8. A method as in claim 7 wherein said biocidally effective amount is in the range of about 50 to about 200 parts by weight of 1,3-dibromo-5,5-dimethylhydantoin per million parts by weight of water.

9. A method as in claim 6 wherein said at least one 1,3-dibromo-5,5-dialkylhydantoin used in forming said microbiocidal solution is at least one 1,3-dibromo-5,5-dialkylhydantoin in which one of the alkyl groups is a methyl group and the other alkyl group contains in the range of 1 to about 4 carbon atoms.

10. A method as in claim 6 wherein the microbiocidal solution used in said contacting is formed from water and a biocidally effective amount of said 1,3-dibromo-5,5-dialkylhydantoin in the range of about 50 to about 100 parts by weight of 1,3-dibromo-5,5-dimethylhydantoin per million parts by weight of water, and wherein said at least one 1,3-dibromo-5,5-dialkylhydantoin used in forming said microbiocidal solution is 1,3-dibromo-5,5-dimethylhydantoin.

11. A method as in claim 6 wherein at least one raw meat product is subjected to said contacting and is rinsed with water within at least 5 minutes after said contacting.

12. A method as in claim 6 wherein said at least one raw meat product is a cut of raw beef which is not darkened by said contacting.

13. A method as in claim 1 wherein C) is conducted.

14. A method as in claim 1 wherein D) is conducted.

15. A method as in claim 1 wherein said four-legged slaughter animal is selected from cattle, swine, and sheep.

16. A method as in claim 1 wherein said at least one 1,3-dibromo-5,5-dialkyl-hydantoin used in forming said microbiocidal solution is at least one 1,3-dibromo-5,5-dialkylhydantoin in which one of the alkyl groups is a methyl group and the other alkyl group contains in the range of 1 to about 4 carbon atoms.

17. A method as in claim 1 wherein said at least one 1,3-dibromo-5,5-dialkyl-hydantoin used in forming said microbiocidal solution is 1,3-dibromo-5,5-dimethyl-hydantoin.

18. A method as in claim 1 wherein the microbiocidal solution used in said contacting is formed from water and a biocidally effective amount of said 1,3-dibromo-5,5-dialkylhydantoin in the range of about 0.5 to about 400 parts by weight of 1,3-dibromo-5,5-dimethylhydantoin per million parts by weight of water.

19. A method as in claim 1 wherein (I) a carcass of a four-legged slaughter animal and/or a raw meat product derived from said carcass, and/or a processed meat product derived from said carcass is contacted at least once with a microbiocidal solution formed from mixing together at least (i) water and (ii) at least one 1,3-dibromo-5,5-dialkylhydantoin, and (II) said carcass, raw meat product derived from said carcass, and/or processed meat product derived from said carcass is subjected to at least one decontamination process selected from ionizing radiation, UV radiation, microwaves, pulsed light, electric fields, hydrostatic pressure, sonication, infra-red radiation, ozonization, and ozone washing, (I) and (II) being conducted in any sequence and/or concurrently.

20. A method of decreasing microbial contamination of a carcass of a four-legged slaughter animal, which method comprises at least contacting said carcass with an aqueous biocidal composition at least once before, during and/or after removal of hide, hair, bristles, or skin from the carcass, said composition comprising a microbiocidally-effective product solution of at least one 1,3-dibromo-5,5-dialkylhydantoin and water.

21. A method of processing raw meat products and/or processed meat products derived from slaughtered animal(s), which method comprises contacting said raw met product or processed meat product with an aqueous microbiocidal composition formed by mixing at least one 1,3-dibromo-5,5-dialkylhydantoin with water in amounts in the range of about 0.5 to about 400 parts by weight of 1,3-dibromo-5,5-dialkylhydantoin per million parts by weight of water, and washing the resultant so-treated product with fresh water.

22. A method as in claim 21 wherein said amounts are in the range of about 50 to about 200 parts by weight of 1,3-dibromo-5,5-dialkylhydantoin per million parts by weight of water.

23. A method as in claim 21 wherein said amounts are in the range of about 50 to about 100 parts by weight of 1,3-dibromo-5,5-dialkylhydantoin per million parts by weight of water.

24. A method as in claim 21 wherein (i) raw meat cuts or (ii) ground or sliced meat products are processed and wherein said amounts are in the range of about 0.5 to about 100 parts by weight of 1,3-dibromo-5,5-dialkylhydantoin per million parts by weight of water.

25. A method as in claim 24 wherein said amounts are in the range of about 0.5 to about 50 parts by weight of 1,3-dibromo-5,5-dialkylhydantoin per million parts by weight of water.

* * * * *

UNITED STATES PATENT AND TRADEMARK OFFICE
CERTIFICATE OF CORRECTION

| | |
|---|---|
| PATENT NO. | : 8,033,898 B2 |
| APPLICATION NO. | : 13/029932 |
| DATED | : October 11, 2011 |
| INVENTOR(S) | : James L. McNaughton et al. |

It is certified that error appears in the above-identified patent and that said Letters Patent is hereby corrected as shown below:

Claims

Column 26, line 20, Claim 21 reads met and should read -- meat --.

Signed and Sealed this
Eleventh Day of August, 2015

Michelle K. Lee
*Director of the United States Patent and Trademark Office*